United States Patent [19]

Farooq

[11] 4,103,032
[45] Jul. 25, 1978

[54] METHOD OF COMBATTING FUNGI AND PSEUDOMONAS SOLANACERUM

[75] Inventor: Saleem Farooq, Aesch, Switzerland

[73] Assignee: Ciba-Geigy Corporation, Ardsley, N.Y.

[21] Appl. No.: 771,865

[22] Filed: Feb. 25, 1977

[30] Foreign Application Priority Data

Mar. 4, 1976 [CH] Switzerland .................. 2700/76

[51] Int. Cl.$^2$ ............................................. A61K 31/09
[52] U.S. Cl. ........................................ 424/341; 71/3; 71/124; 260/613 R
[58] Field of Search ................. 260/613 R; 71/3, 124; 424/341

[56] References Cited

U.S. PATENT DOCUMENTS

| 2,581,917 | 1/1952 | Kitchen | 260/613 R |
| 3,946,084 | 3/1976 | Karrer | 260/613 R |

Primary Examiner—Bernard Helfin
Attorney, Agent, or Firm—Frederick H. Rabin

[57] ABSTRACT

4-Isobornyloxy-allyloxybenzene is disclosed as active ingredient to combat plant diseases caused by *Pseudomonas solanacearum*.

2 Claims, No Drawings

METHOD OF COMBATTING FUNGI AND PSEUDOMONAS SOLANACERUM

The present invention relates to 4-isobornyloxy-allyloxybenzene of the formula I

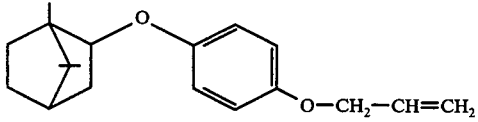

to processes for producing it, and to processes and compositions for combating Pseudomonas solanacearum.

The compound of the formula I can be produced by a process A comprising (i) reacting camphene of the formula II

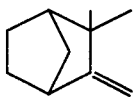

with hydroquinonemonobenzyl ether of the formula III

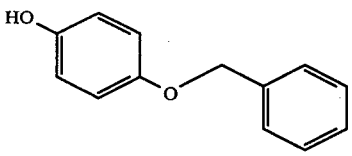

(ii) hydrogenating the resulting 4-isobornyloxy-benzyloxybenzene of the formula IV

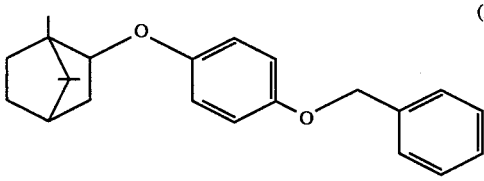

with the splitting-off of toluene; and (iii) reacting the resulting 4-isobornyloxy-phenol of the formula V

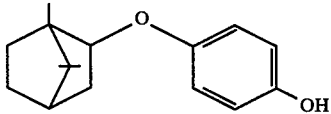

with a compound of the formula VI

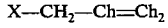

wherein X represents halogen, particularly bromine. [By halogen is meant fluorine, chlorine, bromine or iodine.]

The compound of the formula I can however also be produced by a process B comprising reacting directly camphene of the formula II with hydroquinonemonoallyl ether of the formula VII

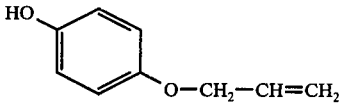

The compound of the formula I contains in the isobornyl ring three asymmetric carbon atoms. The pure optical isomers can be produced by methods known per se, e.g. by conversion of the pair of enantiomers of (V) into a mixture of diastereoisomers (by reaction of (V) with an optically active reagent) and separation of the two diastereoisomers by virtue of their different physical properties (e.g. fractional crystallisation, thin-layer of column chromatography). The separated diastereoisomers obtained in this way can then be split to form the pure enantiomers of (V). It is then possible under controlled conditions (see iii) to convert the separate enantiomers of (V) into the corresponding enantiomers of (I). If no specific synthesis for the isolation of pure isomers is performed, the product is usually obtained as a mixture of the isomers.

The reactions A(i) and B are performed in the presence of Lewis acids, e.g. $BF_3$, $PBr_3$, $AlBr_3$, $AlCl_3$, as well as the halides of As, Sb, Bi, Fe, Zn and Sn, or in the presence of mineral acids such as hydrohalic acids, sulphuric acid, etc. Solvents which can be used are, e.g., hydrocarbons (such as benzene, toluene or xylene), halogenated hydrocarbons (such as methylene chloride and chlorobenzene), ethers (such as diethyl ether, tetrahydrofuran or dioxane), etc. The temperatures are between +10° and −100° C, preferably between 0° and +5° C. The reactions are performed under normal pressure.

The reaction A(ii) is performed in the presence of a hydrogenation catalyst, such as palladium/charcoal (5%), Raney nickel or platinum/platinum oxide; and in solvents such as alcohol (e.g. methanol or ethanol), ethers (e.g. dioxane or tetrahydrofuran), esters (e.g. ethyl acetate), amides (e.g. dimethylformamide) or organic acids (e.g. glacial acetic acid).

The temperatures are between 20° and 100° C; the reaction is preferably performed at room temperature; it is carried out at a pressure of between 1 and 10 atmospheres, preferably however under normal pressure.

The reaction A(iii) is performed in the presence of bases such as hydroxides and carbonates of alkali metals and alkaline-earth metals, or in the presence of organic bases, e.g. pyridine, 2,6-dimethylpyridine or triethylamine; and in solvents such as alcohols (e.g. ethanol or methanol), ethers (e.g. glycol monomethyl ether), amines and amides such as HMPTA, dimethylformamide, or ketones (e.g. acetone or diethyl ketone).

The temperatures are between 0° and 100° C, preferably between 0° C and 50° C. The reaction is performed under normal pressure.

The diseases caused by Pseudomonas solanacearum, such as bacterial wilt of solanaceae, e.g. known as slime disease and as brown rot of potatoes and Granville wilt of tobacco, or "Moko" of bananas, play an important part particularly in the tropics and subtropics, but also in Japan and in the southern states of the U.S.A. This feared bacterial disease is to be found on many families of plants. A possibility of chemical control has not hitherto existed.

It has now been found that surprisingly the compound of the formula I has a very good action against Pseudomonas solanacearum.

Furthermore, the compound of the formula V has a certain fungicidal action in particular against *Erysiphe spp.*

In order to adapt the compound of the formula I to suit the given circumstances and to broaden its sphere of action, it can be used with other suitable pesticides, such as fungicides, insecticides or acaricides, or with the active substances influencing plant growth.

The compound of the formula I can be used on its own or together with suitable carriers and/or additives. Suitable carriers and additives may be solid or liquid, and they correspond to the substances common in formulation practice, such as natural or regenerated substances, solvents, dispersing agents, wetting agents, adhesives, thickeners, binders and/or fertilisers. Such compositions can be produced in a manner known per se by the intimate mixing and grinding of the constituents.

For application, the compound of the formula I can be in the following forms:

solid preparations: dusts, scattering agents, grains or granules (coated granules, impregnated granules and homogeneous granules);
liquid preparations:
 a. water-dispersible concentrates of active substance: wettable powders, pastes, emulsions or solution concentrates;
 b. solutions: aerosols.

The content of active substance in the described compositions is between 0.1 and 95%. The active substance of the formula I can be formulated for example as follows:

Dusts

The following substances are used to produce a) a 5% dust and b) a 2% dust:

a. 5 parts of 4-isobornyloxy-allyloxybenzene,
 95 parts of talcum;
b. 2 parts of Active Substance I,
 1 part of highly dispersed silicic acid,
 97 parts of talcum.

The active substance is mixed and ground with the carriers and in this form can be applied by dusting.

Granulate

The following substances are used to produce a 5% granulate:

5 parts of Active Substance I,
0.25 parts of epichlorohydrin,
0.25 part of cetyl polyglycol ether,
3.50 parts of polyethylene glycol,
91 parts of kaolin (particle size 0.3–0.8 mm).

The active substance is mixed with epichlorohydrin and dissolved with 6 parts of acetone; the polyethylene glycol and cetyl polyglycol ether are then added. The solution obtained is sprayed onto kaolin, and the acetone is then evaporated off in vacuo. A microgranulate of this kind is suitable, e.g., for application to the soil.

Wettable powders

The following constituents are used to produce (a) a 70%, (b) a 40%, (c) and (d) a 25% and (e) a 10% wettable powder:

a. 70 parts of Active Substance I,
 5 parts of sodium dibutyl-naphthalene sulphonate,
 3 parts of naphthalenesulphonic acid/phenolsulphonic acid/formaldehyde condensate 3:2:1,
 10 parts of kaolin,
 12 parts of Champagne chalk;
b. 40 parts of Active Substance I,
 5 parts of sodium lignin sulphonate,
 1 part of sodium dibutyl-naphthalene sulphonate,
 54 parts of silicic acid;
c. 25 parts of 4-isobornyloxy-allyloxybenzene,
 4.5 parts of calcium lignin sulphonate,
 1.9 parts of Champagne chalk/hydroxyethyl cellulose mixture (1:1),
 1.5 parts of sodium dibutyl-naphthalene sulphonate,
 19.5 parts of silicic acid,
 19.5 parts of Champagne chalk,
 28.1 parts of kaolin;
d. 25 parts of 4-isobornyloxy-allyloxybenzene,
 2.5 parts of isooctylphenoxy-polyoxyethylene-ethanol,
 1.7 parts of Champagne chalk/hydroxyethyl cellulose mixture (1:1),
 8.3 parts of sodium aluminium silicate,
 16.5 parts of kieselguhr,
 46 parts of kaolin;
e. 10 parts of Active Substance I,
 3 parts of a mixture of the sodium salts of saturated fatty alcohol sulphates,
 5 parts of naphthalenesulphonic acid/formaldehyde condensate,
 82 parts of kaolin.

The active substance is intimately mixed in suitable mixers with the additives, and the mixture is then ground in the appropriate mills and rollers. There are obtained wettable powders which have excellent wetting and suspension properties, and which can be diluted to form suspensions of the required concentration and used, for example, for leaf application.

Emulsifiable concentrates

The following substances are used to produce a 25% emulsifiable concentrate:

25 parts of Active Substance,
2.5 parts of epoxidised vegetable oil,
10 parts of an alkylarylsulphonate/fatty alcohol polyglycol ether mixture,
5 parts of dimethylformamide,
57.5 parts of xylene.

Emulsions of the desired concentration can be produced from this concentrate by dilution with water.

The following Examples serve to further illustrate the invention without limiting the scope thereof. The temperature values are given in degrees Centigrade.

EXAMPLE 1 a. Production of 4-isobornyloxy-benzyloxybenzene (compound of the formula IV)

500 g (2.5 moles) of hydroquinonemonobenzyl ether was added to a solution (cooled to 0°–5°) of 340 g (2.5 moles) of (+)-camphene in 1660 ml of toluene. To this reaction mixture was added dropwise, in the course of 2 hours, 33.6 g of boron trifluoride etherate, and stirring was subsequently maintained at 0°–5° for 2 hours. The reaction mixture was filtered and the filtrate was washed three times with 500 ml of 10% potassium hydroxide solution each time, and four times with 500 ml of saturated sodium chloride solution each time. The organic phase was dried over sodium sulphate, filtered off, and concentrated by evaporation under reduced pressure. The crude product was crystallised from ethanol to obtain the product of the formula IV having a melting point of 85°.

b. Production of 4-isobornyloxy-phenol (compound of the formula V)

34 g. (0.1 mole) of 4-isobornyloxy-benzyloxybenzene, dissolved in 350 ml of ethanol, was hydrogenated with the use of 3.4 g of Pd—C (5%) as catalyst with 2.38 liters (105%) of hydrogen at normal pressure. The reaction mixture was filtered through Hyflo and freed at reduced pressure from the solvent. Distillation of the crude product at 134° C / 0.09 mm Hg yielded the desired substance of the formula V having a melting point of 72°.

c. Production of 4-isobornyloxy-allyloxybenzene (compound of the formula I 61 ml of a 1N ethanolic potassium hydroxide solution was added dropwise at room temperature, within 30 minutes, to a solution of 15 g (0.061 mole) of 4-isobornyloxy-phenol, 10 g (0.083 mole) of allyl bromide in 80 ml of monoglyme. The reaction mixture was subsequently stirred for 12 hours at room temperature, the precipitated potassium bromide was filtered off and the filtrate freed under reduced pressure from the solvent. The residue was taken up in 100 ml of ether, and washed twice with 50 ml of saturated sodium chloride solution each time. The organic phase was dried over sodium sulphate, filtered off and concentrated under reduced pressure. The crude product was crystallised from hexane to obtain the compound of the formula I having a melting point of 48°–52°.

EXAMPLE 2: Biological activity

A. Bactericide

After 3 weeks' cultivation in a greenhouse, 6 tomato plants of the "Bonnie Best" variety were watered with a suspension of the test substance of the formula I. The concentration of the suspension was such that the amount of test substance in the pot soil attained a level of 100 ppm of active substance. Two days after this treatment, there was carried out an artifical infestation of the plants by an injuring of the roots with a sharp knife and the watering thereof with a bacterial suspension of Pseudomonas solanacearum. At the end of 10 days' incubation at 30° C with high humidity, massive disease symptoms (wilted leaves, watery-rotten stems with bacterial slime drops thereon, with a subsequent complete withering of the plants) were evident on the untreated control plants, whereas the treated plants remained to a great extent healthy.

An evaluation was made according to the following ratings:

0 = plants completely healthy,
1 = dark brown discolouration of vascular bundles,
2 = wilted leaves,
3 = plants dead.

In several repeats according to the above procedure, ratings of between 0 and 0.5 were obtained.

B. Fungicide

Barley plants about 8 cm in height were sprayed with a spray liquor (0.02% of active substance) produced from a wettable powder of the active substance of the formula V. After 48 hours, the treated plants were dusted with conidia of the fungus Erysiphe graminis. The infested barley plants were kept in a greenhouse at about 22° C and the fungus infestation was assessed after 10 days.

Compared with infested but untreated control plants, the plants treated with active substance were infested to the extent of less than 5%.

I claim:

1. A method for combatting Pseudomonas solanacearum on growing plants comprising applying thereto a bactericidally effective amount of 4-isobornyloxy-allyloxybenzene.

2. A method for combatting phytopathogenic fungi which comprises applying to growing plants a fungicidally effective amount of 4-isobornyloxy-allyloxybenzene.

* * * * *